(12) United States Patent
Braud

(10) Patent No.: US 9,827,071 B2
(45) Date of Patent: Nov. 28, 2017

(54) INTRAORAL PROTECTION

(71) Applicant: MO 205, La Rochelle (FR)

(72) Inventor: Vincent Braud, La Rochelle (FR)

(73) Assignee: MO 205, La Rochelle (FR)

( * ) Notice: Subject to any disclaimer, the term of this patent is extended or adjusted under 35 U.S.C. 154(b) by 0 days.

(21) Appl. No.: 14/410,030

(22) PCT Filed: Jun. 10, 2013

(86) PCT No.: PCT/FR2013/000145
§ 371 (c)(1),
(2) Date: Dec. 19, 2014

(87) PCT Pub. No.: WO2014/001655
PCT Pub. Date: Jan. 3, 2014

(65) Prior Publication Data
US 2015/0190211 A1    Jul. 9, 2015

(30) Foreign Application Priority Data

Jun. 26, 2012 (FR) .................... 12 01799

(51) Int. Cl.
*A61C 5/00* (2017.01)
*A61C 5/12* (2006.01)
*A61C 5/88* (2017.01)
*A61C 5/90* (2017.01)

(52) U.S. Cl.
CPC ............. *A61C 5/127* (2013.01); *A61C 5/88* (2017.02); *A61C 5/90* (2017.02)

(58) Field of Classification Search
CPC ................. A61C 5/127; A61C 5/14
USPC ............ 433/140, 29, 91, 93, 136, 137, 138
See application file for complete search history.

(56) References Cited

U.S. PATENT DOCUMENTS

| 5,730,599 A | 3/1998 | Pak |
| 6,022,214 A * | 2/2000 | Hirsch ............ A61B 1/24 433/140 |
| 2003/0134253 A1 | 7/2003 | Hirsch et al. |

FOREIGN PATENT DOCUMENTS

KR    100654392 B1 * 11/2006

OTHER PUBLICATIONS

International Search Report dated Sep. 19, 2013 for PCT Application No. PCT/FR2013/000145.

* cited by examiner

*Primary Examiner* — Eduardo C Robert
*Assistant Examiner* — Mirayda A Aponte
(74) *Attorney, Agent, or Firm* — Miles & Stockbridge P.C.

(57) ABSTRACT

An oral protection device including a dental wedge to be positioned between the dental arches of one side of the mouth, and a protection blade having a first portion which pushes against the tongue, and a second portion which engages with the other side of the mouth within the vestibule and having a blade extended by a turned-back section which forms a hook positioned at the labial commissure of the mouth.

10 Claims, 3 Drawing Sheets

INTRAORAL PROTECTION

BACKGROUND OF THE INVENTION

The invention relates to a device for protecting the mouth during work on the teeth.

During work on teeth, the patient must keep his mouth open. The surgeon can then access the teeth in order to work on them, taking care not to injure the inside of the cheek and/or the tongue.

Therefore, in order to access the teeth, the patient must keep his mouth open, which he does. However, if the surgery is lengthy, the jaws gradually close since keeping the mouth open for a long period is not easy.

The first problem is therefore keeping the mouth open.

The second problem is avoiding injuring the tongue and/or the inside of the cheek.

One old technique, still used, consists of separating the cheek and tongue with cylindrical cotton pads that are placed on either side of the working area and/or between the dental arches.

This technique has been improved by devices that push the tongue towards the rear and hold the mouth open.

To keep the mouth open, there therefore exist devices comprising a thick wedge that is positioned between the interdental arches on the side opposite to the one where the tooth to be treated is located.

In order to protect the mouth, using a blade that is attached to the aforementioned thick wedge and positioned so as to push the tongue behind the blade is known (US 2003/134253 or U.S. Pat. No. 5,730,599).

This blade comprises a part that pushes the tongue, which is connected to a side flap that bears on the other side of the mouth, being positioned between the cheek and the teeth in the vestibule. The blade, deployed flat, forms in front view a kind of eight on its side.

So that this blade is positioned correctly and remains in place, the connection between the dental wedge and the blade is rigid so that it is the positioning of the wedge that orients the blade. The rigidity of the connection is constraining in the design of the device and in the positioning since each mouth is particular whereas the device is of a standard type.

The invention aims to do a solution to the problems mentioned above.

SUMMARY OF THE INVENTION

To this end, the subject matter of the invention is an oral protection device comprising a dental wedge intended to be positioned between the dental arches on one side of the mouth, a protective blade comprising a first part pushing the tongue and a second part coming into abutment on the other side of the mouth, this device being characterised in that the second part of the blade is extended by a return in order to form a hook positioned at the corner of the lips.

For example, embodiments of such an oral-protection device can include a dental wedge adapted to be positioned between dental arches on one side of a user's mouth, and a protective blade having a first part constructed to exert a force against the user's tongue and a second part connected at a first side to said first part and constructed to contact another side of the user's mouth between the user's cheek and teeth when the oral-protection device is disposed in a fully-installed position within the user's mouth. The second part of the protective blade extends adjacently to the first part along internal surfaces of the user's cheek and the second part is extended by a return section constructed to engagingly contact with the user's outer cheek when the oral-protection device is disposed in a fully-installed position within the user's mouth. The return section forms, with the second part of the protective blade, a hook positioned at a corner of the user's lips when the oral-protection device is disposed in a fully-installed position within the user's mouth, and the hook wraps around an external portion of the user's cheek at the corner of the user's lips and has a tip end which extends in a backward direction toward the back of the user's head when the oral-protection device is disposed in a fully-installed position within the user's mouth.

BRIEF DESCRIPTION OF THE DRAWINGS

The invention will be clearly understood by means of the description given below by way of non-limitative example, with regard to the drawing, which shows.

DETAILED DESCRIPTION

Figure 1:
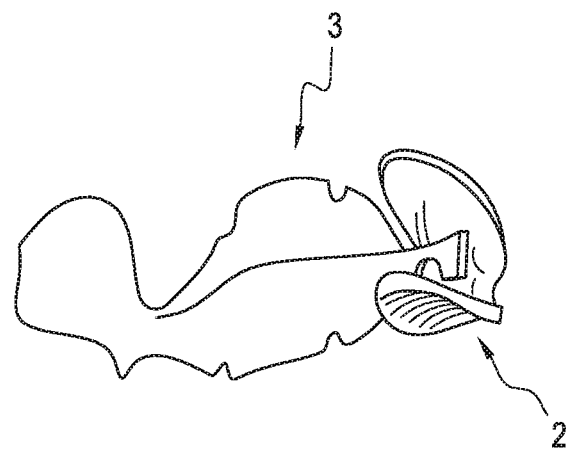
FIG. 1: the protective device seen in perspective
Figure 2:
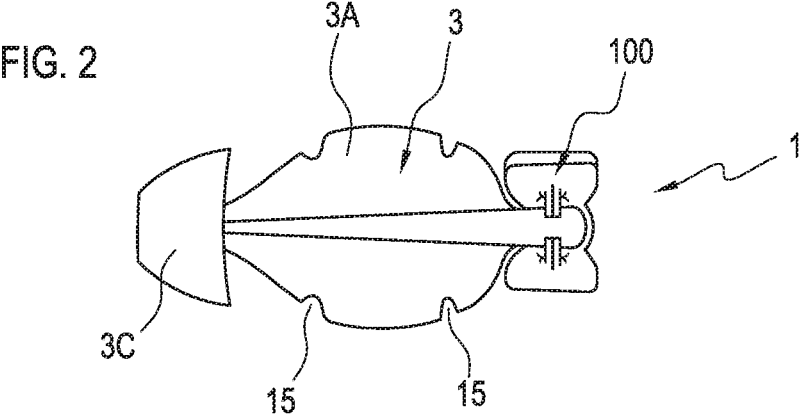
FIG. 2: the device of FIG. 1 seen in front view
Figure 3:
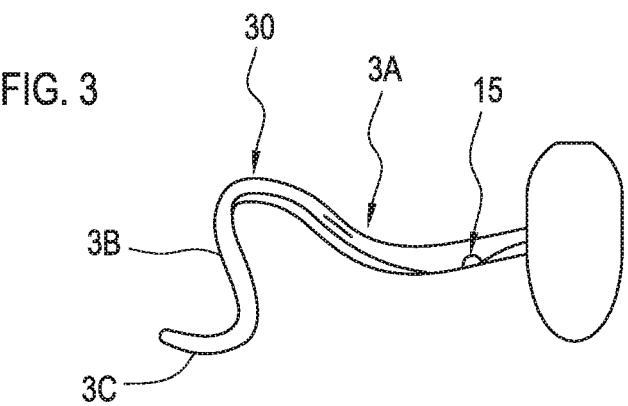
FIG. 3: the device of FIG. 1 seen from above
Figure 4:
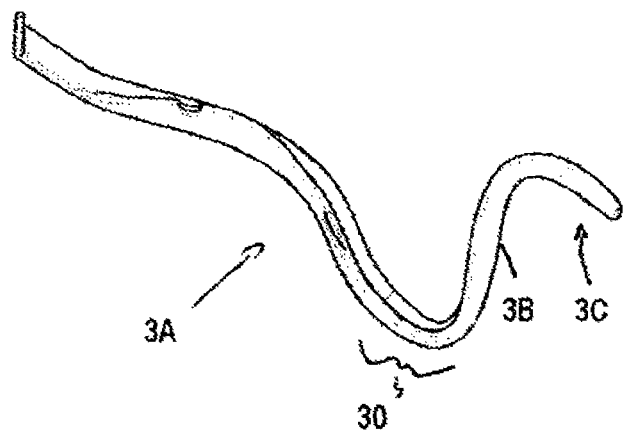
FIG. 4: the blade of the device of FIG. 1 alone
Figure 5:
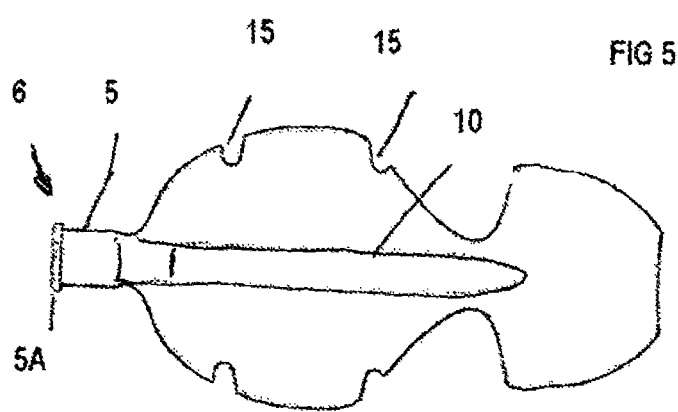
FIG. 5: the blade of FIG. 4 seen in front view
Figure 6:
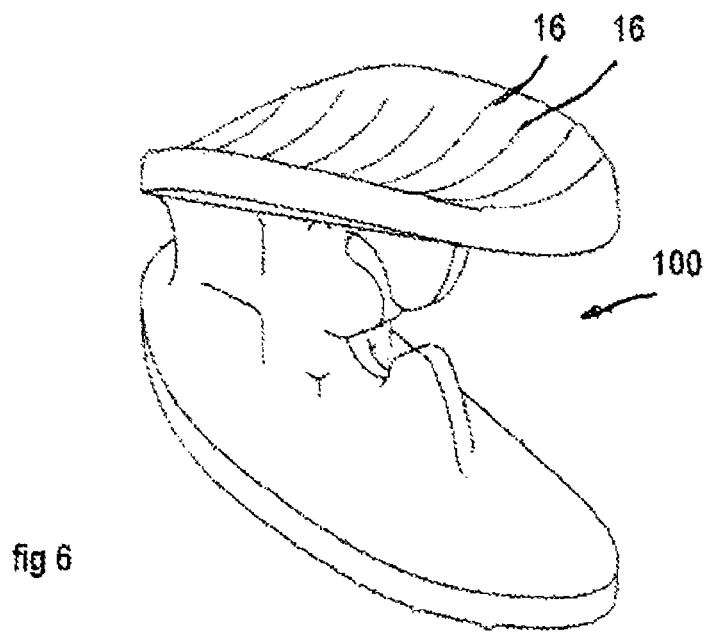
FIG. 6: the wedge alone in perspective
Figure 7:
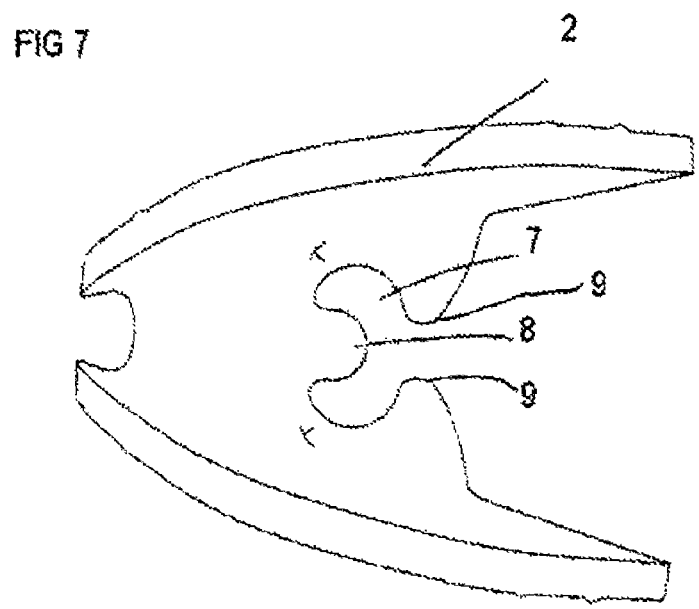
FIG. 7: the wedge of FIG. 6 in side view

Referring to the drawing, a oral-protection device 1 can be seen, which is used for dental work. This device is intended to keep the mouth of the patient open and for this purpose a wedge 2 is used the height of which and the position of which at the dental arches determines the opening of the mouth.

With this wedge there is associated a protective blade 3 comprising a first part 3A and second part 3B coming into abutment on the other side of the mouth, this device being characterised in that the second part 3B of the blade is extended by a return 3C intended to bear on the outer cheek in order to form a hook positioned at the corner of the lips.

The hook is turned towards the rear.

When the device is positioned, it is held at both ends. It is therefore immobilised on the one hand by the wedge between the jaws and on the other hand by the hook which, formed by the second part 3B and the return 3C, is engaged with the cheek.

There is therefore a secure positioning.

The first part 3A pushes the tongue and protects it, while the second part 3B protects the cheek by sliding between the cheek and the teeth, this region being referred to as the vestibule.

In addition, the first part 3A of the blade has a height greater than the distance between the floor of the mouth and the palate, which forces the blade to bend when it is positioned, and therefore this "crushing" increases the holding. Between the various parts of the blade, there is a reduction in material in order to be able to orient parts with respect to one another. It should be noted that the reduction 30 between the first part 3A of the blade and the second part 3B makes it possible to be positioned behind the molars and to obtain wedging by gripping.

Putting into practice begin with the positioning of the hook and then the position of the wedge.

This return does not serve for protection but makes it possible to replace a rigid connection between the blade and the wedge with a flexible connection 100 of the rapid-fitting type with clearance facilitation the orientation of the blade with respect to the wedge. The connection is made on the front face of the wedge, that is to say the face of the wedge opposite to the bottom of the mouth.

The connection 100 between the wedge and the blade is as follows:

The blade 3 comprises a male piece 5 in the form of a C-shaped profile, the concavity 6 of the C being oriented towards the wedge, this profile coming to fit in a complementary cavity 7 with a deformable opening for the forcible passage of the C. The cavity 7 receiving the C-shaped profile is situated in front of the wedge.

When the blade is associated with the wedge, the concavity 6 of the profile covers a rim 8. This C-shaped profile can move slightly angularly with respect to this rim and consequently enable the blade 3 to be oriented. The wedge therefore has an elasticity enabling the C-shaped profile to be mounted by elastic deformation of the wedge by opening the lips 9, which reduce the entry of the cavity. Mounting this blade allows rotational and translation adjustments of the blade with respect to the wedge. Adjustment is facilitated since the other end of the blade is positioned at the corner of the lips.

The wedge is therefore elastically deformable in compression and has two opposite support regions for the teeth.

This elasticity (which remains low) of the wedge has another advantage for the patient, who can bite on the wedge without receiving an unpleasant sensation and, in biting this wedge, he grips the C-shaped profile, which locks.

The free end of this shape in a half-tube (C-shaped profile) has a stop 5A that limits the axial movement of said profile in the open cavity 7 of the wedge. The half-tube shape can slide within the limit of the length thereof.

A rapid, adjustable and flexible fixing has therefore been achieved.

This half-tube (hollow semi-cylinder) shape located on the side of the blade in order to constitute one of the two complementary parts of a means of connection with the wedge is extended substantially as far as the end of the second part of the blade in front of the return, thus forming a longitudinal rib 10 that gives the blade a rigidity in its longitudinally corrugated form.

If the device is looked at, the first part 3A is in the form of an elongate leaf which, after broadening, narrows as it moves away from the wedge in order to be extended by a transition region 30 that is curved and positions the second part 3B in a direction of around 90° with respect to the first part and this second part is extended by a return 3C in order to form a hook.

The blade has a curved face, the concavity of which is oriented forwards and therefore towards the entrance of the mouth. The choice of the variations in blade thicknesses and their locations confers greater or lesser flexibility on this blade.

The presence of notches 15 will be noted on the edge of the blade to enable fluids to flow, which will be aspirated by a means that is not shown.

As stated, the wedge is compressive and therefore not strictly rigid. Ribs 16 at the abutment regions prevent sliding along the longitudinal axis of the wedge. The abutment regions are also concave in the transverse axis in order to transversely limit the movement of the teeth and therefore to position said teeth.

The demountable connection between the wedge of the blade allows rapid removal and separate treatment of the elements constituting the device for better sterilisation.

The material of the wedge may be of a different nature from that of the blade so that each piece can be moulded individually, which avoids moulding stresses if bi-injection is carried out.

It makes it possible to choose one wedge from a set of wedges and one blade from a set of blades of different sizes. Each piece is sterilisable.

The invention claimed is:

1. An oral-protection device comprising:
   a dental wedge adapted to be positioned between dental arches on one side of a user's mouth; and
   a protective blade comprising a first part constructed to exert a force against the user's tongue and a second part connected at a first side to said first part and constructed to contact another side of the user's mouth between the user's cheek and teeth when said oral-protection device is disposed in a fully-installed position within the user's mouth,
   wherein the second part of the protective blade extends adjacently to the first part along internal surfaces of the user's cheek and said second part is extended by a return section constructed to engagingly contact with the user's outer cheek when said oral-protection device is disposed in a fully-installed position within the user's mouth,
   wherein said return section forms, with said second part of the protective blade, a hook positioned at a corner of the user's lips when said oral-protection device is disposed in a fully-installed position within the user's mouth, and
   where said hook wraps around an external portion of the user's cheek at the corner of the user's lips and has a tip end which extends in a backward direction toward the back of the user's head when said oral-protection device is disposed in a fully-installed position within the user's mouth.

2. The oral-protection device according to claim 1, wherein the first part of the protective blade has a height greater than a distance between a floor of the user's mouth and a palate, such that the protective blade bends and thus increases a holding ability provided by said force.

3. The oral-protection device according to claim 1, wherein the protective blade is associated with the dental wedge through a flexible connection of rapid-fitting type with a clearance constructed to facilitate an orientation of the protective blade with respect to the wedge.

4. The oral-protection device according to claim 3, wherein the flexible connection comprises a male piece having a C-shaped profile,
   wherein a concavity of the C-shaped profile is oriented towards the wedge, and
   wherein the C-shaped profile is adapted to fit in a complementary cavity in the wedge with a deformable opening for forcible passage of the C-shaped profile.

5. The oral-protection device according to claim 4, wherein a length of the C-shaped profile enables said profile to move in translation in the cavity that accepts it.

6. The oral-protection device according to claim 4, wherein the concavity of the C-shaped profile covers a rim on the wedge.

7. The oral-protection device according to claim 1, wherein the wedge is elastically deformable by compression and has a plurality of opposing abutment regions for teeth.

8. The oral-protection device according to claim 7,
wherein the plurality of abutment regions for teeth have ribs that prevent sliding along a longitudinal axis of the wedge, and
wherein each said abutment region is also concave in a transverse axis to position the teeth transversely.

9. The protective device according to claim 1,
wherein the first part of the protective blade is in the form of an elongate leaf that narrows in a direction extending away from the wedge in order to be extended by a transition region that is curved, and that positions the second part of the protective blade in a direction of around 90° with respect to the first part, and
wherein the second part is extended by a return in order to form a hook.

10. The protective device according to claim 9,
wherein a reduction in material between the first part of the protective blade and the second part allows positioning behind the user's molars and obtains wedging by gripping.

* * * * *